(12) United States Patent
O'Sullivan et al.

(10) Patent No.: US 8,455,663 B2
(45) Date of Patent: Jun. 4, 2013

(54) HALOSUBSTITUTED ARYLOXYALKYLIMIDAZOLINES FOR USE AS PESTICIDES

(75) Inventors: Anthony Cornelius O'Sullivan, Stein (CH); Thomas Pitterna, Stein (CH); Jürgen Harry Schaetzer, Stein (CH); Christoph Luethy, Münchenstein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 414 days.

(21) Appl. No.: 12/677,825

(22) PCT Filed: Sep. 9, 2008

(86) PCT No.: PCT/EP2008/007363
§ 371 (c)(1),
(2), (4) Date: Jun. 29, 2010

(87) PCT Pub. No.: WO2009/036909
PCT Pub. Date: Mar. 26, 2009

(65) Prior Publication Data
US 2010/0280088 A1 Nov. 4, 2010

(30) Foreign Application Priority Data

Sep. 18, 2007 (GB) .................................. 0718196.9
Nov. 6, 2007 (GB) .................................. 0721772.2

(51) Int. Cl.
C07D 233/22 (2006.01)
C07C 255/13 (2006.01)

(52) U.S. Cl.
USPC ................. 548/353.1; 548/334.1; 558/389

(58) Field of Classification Search
USPC ............. 548/353.1, 347.1, 334.1; 558/389
See application file for complete search history.

(56) References Cited

U.S. PATENT DOCUMENTS

| | | | |
|---|---|---|---|
| 4,226,876 A | 10/1980 | Copp et al. | |
| 4,228,175 A | 10/1980 | Boeger et al. | |
| 4,232,011 A | 11/1980 | Boeger et al. | |
| 4,233,306 A | 11/1980 | Boeger et al. | |
| 4,241,075 A | 12/1980 | Drabek et al. | |
| 4,276,302 A * | 6/1981 | Brechbuhler et al. | 514/401 |
| 5,128,361 A | 7/1992 | Stark et al. | |

FOREIGN PATENT DOCUMENTS

| | | |
|---|---|---|
| DE | 2940167 | 4/1980 |
| EP | 0011596 | 5/1980 |
| EP | 0049797 | 4/1982 |
| EP | 1958507 | 8/2008 |
| EP | 1958508 | 8/2008 |
| FR | 2388496 | 11/1978 |
| GB | 2023603 | 1/1980 |
| GB | 1592649 | 10/1980 |
| GB | 1593276 | 7/1981 |
| JP | 51106739 | 9/1976 |

* cited by examiner

*Primary Examiner* — Jason M Nolan
(74) *Attorney, Agent, or Firm* — Brian McAlhaney

(57) ABSTRACT

The present invention relates to novel imidazoline derivatives and their use as insecticidal, acaricidal, molluscicidal and nematocidal agents. The invention also extends to insecticidal, acaricidal, molluscicidal and nematicidal compositions comprising such imidazoline derivatives, and to methods of using such derivatives and/or compositions to combat and control insect, acarine, mollusc and nematode pests. A compound of formula (I) and salts and N-oxides thereof, wherein: $R^1$ is $C_{1-10}$ alkyl; $R^2$ is chloro, bromo or iodo; $R^3$ is $C_{2-5}$ alkyl, $C_{1-5}$ haloalkyl, $C_{1-6}$ hydroxyalkyl, $C_{1-5}$alkoxy-$(C_{1-3})$-alkyl, di-$(C_{1-5}$ alkoxy)-$(C_{1-3})$-alkyl, $C_{1-5}$alkylthio-$(C_{1-3})$-alkyl; $C_{1-5}$ alkylsulfinyl-$(C_{1-3})$alkyl; $C_{2-5}$ alkenyl, $C_{1-5}$ haloalkenyl, $C_{2-5}$ alkinyl, $C_{3-6}$ cycloalkyl, $C_{3-6}$ cycloalkenyl, hydroxy, $C_{1-5}$ alkoxy, $C_{1-5}$haloalkoxy, $C_{1-5}$alkylthio, $C_{1-5}$ haloalkylthio, formyl, cyano, bromo, or iodo; Z is hydrogen, hydroxy, nitro cyano, rhodano, formyl, G-, G-S—, G-S—S—, G-A-, $R^7R^8N$—, $R^7R^8N$—S—, $R^7R^8N$-A-, G-O-A-, G-S-A-, $(R^{10}O)(R^{11}O)P(X)$—, $(R^{10}O)(R^{11}S)P(X)$—, $(R^{10}O)(R^{11})P(X)$—, $(R^{10}S)(R^{11}S)P(X)$—, $(R^{10}O)(R^{14}R^{15}N)P(X)$—, $(R^{11})(R^{14}R^{15}N)P(X)$—, $(R^{14}R^{15}N)(R^{16}R^{17}N)P(X)$—, G-N=CH—, G-O—N=CH—, N=C—N=CH—, or Z is a group of formula (II), wherein B is S—, S—S—, S(O)—, C(O)—, or $(CH_2)_n$—; n is an integer from 1 to 6; and $R^1$, $R^2$, and $R^3$ are as defined above; and G is optionally substituted $C_{1-10}$alkyl, optionally substituted $C_{2-10}$ alkenyl, optionally substituted $C_{2-10}$ alkynyl, optionally substituted $C_{3-7}$ cycloalkyl, optionally substituted $C_{3-7}$ cycloalkenyl, optionally substituted aryl, optionally substituted heteroaryl or optionally substituted heterocyclyl; A is S(O), $SO_2$, C(O) or C(S).

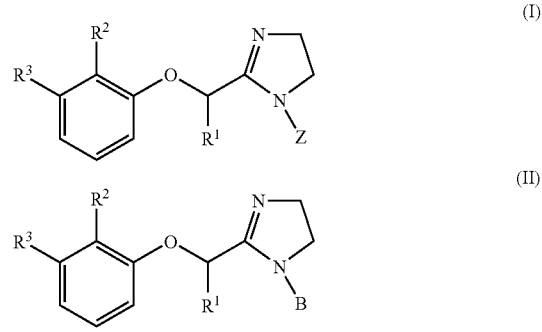

19 Claims, No Drawings

HALOSUBSTITUTED ARYLOXYALKYLIMIDAZOLINES FOR USE AS PESTICIDES

This application is a 371 of International Application No. PCT/EP2008/007363 filed Sep. 9, 2008, which claims priority to GB 0718196.9 filed Sep. 18, 2007, and GB 0721772.2 filed Nov. 6, 2007, the contents of which are incorporated herein by reference.

The present invention relates to novel imidazoline derivatives and their use as insecticidal, acaricidal, molluscicidal and nematocidal agents. The invention also extends to insecticidal, acaricidal, molluscicidal and nematicidal compositions comprising such imidazoline derivatives, and to methods of using such derivatives and/or compositions to combat and control insect, acarine, mollusc and nematode pests.

A number of imidazoline derivatives are known, for example from DE 2756638, DE2818367, and EP0011596, that all disclose phenoxy-methyl- and α-alkyl-phenoxy-methyl-imidazoline derivatives, wherein the phenyl ring is substituted among others with methyl and/or chloro groups. All of these compounds are disclosed to be arthropodicidal, but especially acaricidal and/or ectoparasiticidal. DE3842798 discloses similar compounds for systemic combating ectoparasites in host animals.

Japanese Patent Application No. JP 51106739 discloses phenoxy-methyl-imidazoline derivatives, wherein the phenyl ring is likewise substituted with such groups, and these compounds are disclosed to be active against insects, vermin and parasites, such as ticks, mites, cockroaches and mosquitoes. However none of these compounds bear a halogen atom in the 2-position in combination with a further substituent in the 3-position of the phenoxy moiety.

We have now found that phenoxyimidazoline derivatives that bear an halogen atom in the 2-position in combination with a further substituent in the 3-position of the phenoxy moiety have surprisingly good pesticidal activity, especially against insects, and in particular against insects of the order hemiptera.

Thus according to a first aspect of the present invention there is provided a compound of formula (I)

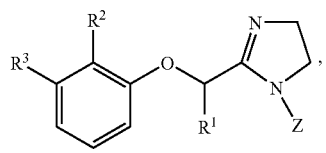

(I)

and the salts and N-oxides thereof, wherein:
$R^1$ is $C_{1-10}$ alkyl;
$R^2$ is chloro, bromo or iodo;
$R^3$ is $C_{2-5}$ alkyl, $C_{1-5}$ haloalkyl, $C_{1-6}$ hydroxyalkyl, $C_{1-5}$ alkoxy-($C_{1-3}$)-alkyl, di-($C_{1-5}$ alkoxy)-($C_{1-3}$)-alkyl, $C_{1-5}$ alkylthio-($C_{1-3}$)-alkyl; $C_{1-5}$alkylsulfinyl-($C_{1-3}$)-alkyl; $C_{2-5}$ alkenyl, $C_{1-5}$ haloalkenyl $C_{2-5}$ alkinyl, $C_{3-6}$ cycloalkyl, $C_{3-6}$ cycloalkenyl, hydroxy, $C_{1-5}$ alkoxy, $C_{1-5}$ haloalkoxy, $C_{1-5}$ alkylthio, $C_{1-5}$ haloalkylthio, formyl, cyano, bromo, or iodo;
Z is hydrogen, hydroxy, nitro, cyano, rhodano, formyl, G-, G-S—, G-S—S—, G-A-, $R^7R^8N$—, $R^7R^8N$—S—, $R^7R^8N$-A-, G-O-A, G-S-A-, $(R^{10}O)(R^{11}O)P(X)$—, $(R^{10}O)(R^{11}S)P(X)$—, $(R^{10}O)(R^{11})P(X)$—, $(R^{10}S)(R^{11}S)P(X)$—, $(R^{10}O)(R^{14}R^{15}N)P(X)$—, $(R^{11})(R^{14}R^{15}N)P(X)$—, $(R^{14}R^{15}N)(R^{16}R^{17}N)P(X)$—, G-N═CH—, G-O—N═CH—, N═C—N═CH—, or Z is a group of formula (II)

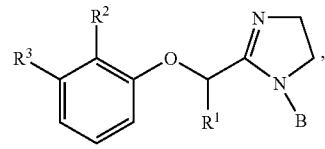

(II)

wherein B is S—, S—S—, S(O)—, C(O)—, or $(CH_2)_n$—; n is an integer from 1 to 6; and $R^1$, $R^2$, and $R^3$ are as defined above; and
G is optionally substituted $C_{1-10}$ alkyl, optionally substituted $C_{2-10}$ alkenyl, optionally substituted $C_{2-10}$ alkynyl, optionally substituted $C_{3-7}$ cycloalkyl, optionally substituted $C_{3-7}$ cycloalkenyl, optionally substituted aryl, optionally substituted heteroaryl or optionally substituted heterocyclyl;
A is S(O), $SO_2$, C(O) or C(S);
$R^7$ and $R^8$ are each independently hydrogen or G; or $R^7$ and $R^8$ together with the N atom to which they are attached form a group N═$CR^{12}R^{13}$; or $R^7$ and $R^8$ together with the N atom to which they are attached form a five, six or seven-membered heterocyclic ring, which heterocyclic ring optionally contains one or two further heteroatoms selected from O, N or S, and is optionally substituted by one or two $C_{1-6}$ alkyl groups;
$R^{10}$ and $R^{11}$ are each independently $C_1$-$C_6$ alkyl, benzyl or phenyl where the phenyl group is optionally substituted with halogen, nitro, cyano, $C_{1-3}$ alkyl, $C_{1-3}$ haloalkyl, $C_{1-3}$ alkoxy, $C_{1-3}$ haloalkoxy;
$R^{12}$, $R^{13}$, $R^{14}$, $R^{15}$, $R^{16}$ and $R^{17}$ are each independently hydrogen or $C_1$-$C_6$ alkyl;
X is O or S.

The compounds of formula (I) may exist in different geometric or optical isomeric or different tautomeric forms. One or more centres of chirality may be present, for example on the chiral carbon atom $CHR^1$ or a chiral carbon unit in the group G, or a chiral —S(O)— unit in the group Z, in which case compounds of the formula (I) may be present as pure enantiomers, mixtures of enantiomers, pure diastereomers or mixtures of diastereomers. There may be double bonds present in the molecule, such as C═C or C═N bonds, in which case compounds of formula (I) may exist as single isomers of mixtures of isomers. Centres of tautomerisation may be present. This invention covers all such isomers and tautomers and mixtures thereof in all proportions as well as isotopic forms such as deuterated compounds.

Suitable acid addition salts include those with an inorganic acid such as hydrochloric, hydrobromic, sulfuric, nitric and phosphoric acids, or an organic carboxylic acid such as oxalic, tartaric, lactic, butyric, toluic, hexanoic and phthalic acids, or sulphonic acids such as methane, benzene and toluene sulphonic acids. Other examples of organic carboxylic acids include haloacids such as trifluoroacetic acid.

N-oxides for example as part of G are oxidised forms of tertiary amines or oxidised forms of nitrogen containing heteroaromatic compounds are included. They are described in many books for example in "Heterocyclic N-oxides" by Angelo Albini and Silvio Pietra, CRC Press, Boca Raton, Fla., 1991.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{10}$ alkyl groups, but are preferably $C_1$-$C_8$, even more preferably $C_1$-$C_6$ and most preferably $C_1$-$C_4$ alkyl groups.

Ring or chain forming alkylene, alkenylene and alkinyl groups can optionally be further substituted by one or more halogen, $C_{1-3}$ alkyl and/or $C_{1-3}$ alkoxy.

When present, the optional substituents on an alkyl moiety (alone or as part of a larger group) include one or more of halogen, nitro, cyano, rhodano, isothiocyanato, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted), $C_{3-7}$ cycloalkyoxy (where the cycloalkyl group is optionally substituted with $C_{1-6}$ alkyl or halogen), $C_{2-10}$ alkenyloxy, $C_{2-10}$ alkynyloxy, mercapto, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$alkyldiarylsilyl, triarylsilyl, aryl($C_{1-4}$alkylthio($C_{1-4}$)alkyl, aryloxy($C_{1-4}$)alkyl, formyl, $C_{1-10}$ alkylcarbonyl, hydroxycarbonyl, $C_{1-10}$ alkoxycarbonyl, aminocarbonyl, $C_{1-6}$ alkylaminocarbonyl, di($C_{1-6}$alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), $C_{1-6}$alkylaminocarbonyloxy, di($C_{1-6}$)alkylaminocarbonyloxy, oximes and oximethers such as =NO—$C_{1-6}$-alkyl, =NO—$C_{1-6}$haloalkyl and =NO—$C_{1-2}$aryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, ($C_{1-6}$) alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{3-6}$ cycloalkylcarbonyl (for example cyclopropylcarbonyl, optionally substituted $C_{2-6}$ alkynylcarbonyl, optionally substituted arylcarbonyl (for example benzoyl) or optionally substituted heteroarylcarbonyl (for example nicotinoyl or isonicotinoyl).

Halogen is fluorine, chlorine, bromine or iodine.

Haloalkyl groups are alkyl groups which are substituted with one or more of the same or different halogen atoms and are, for example, $CF_3$, $CF_2C_1$, $CF_2H$, $CCl_2H$, $CH_2F$, $CH_2Cl$, $CH_2Br$, $CH_3CHF$, $(CH_3)_2CF$, $CF_3CH_2$ or $CHF_2CH_2$.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic preferably monocyclic or bicyclic ring systems containing up to 10 atoms including one or more (preferably one or two) heteroatoms selected from O, S and N. Examples of such rings include 1,3-dioxolane, oxetane, tetrahydrofuran, morpholine, thiomorpholine and piperazine.

When present, the optional substituents on heterocyclyl include $C_{1-6}$ alkyl and $C_{1-6}$ haloalkyl, an oxo-group (allowing one of the carbon atoms in the ring to be in the form of a keto group), as well as those optional substituents given above for an alkyl moiety.

Cycloalkyl includes cyclopropyl, cyclobutyl, cyclopentyl and cyclohexyl. Cycloalkylalkyl is preferentially cyclopropylmethyl. Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, rhodano, isothiocyanato, $C_{1-6}$ alkyl, $C_{1-6}$ haloalkyl, C'" alkoxy-($C_{1-6}$)alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{6-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkyl-silyl($C_{1-6}$)alkoxy, $C_{1-6}$ alkoxycarbonyl($C_{1-10}$)alkoxy, $C_{1-10}$ haloalkoxy, aryl($C_{1-4}$) alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, mercapto, $C_{1-10}$ alkylthio, $C_{1-10}$ haloalkylthio, aryl($C_{1-4}$)alkylthio, $C_{3-7}$ cycloalkylthio (where the cycloalkyl group is optionally substituted with $C_{1-6}$ alkyl or halogen), tri($C_{1-4}$)-alkylsilyl($C_{1-6}$) alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, $C_{1-10}$ alkylcarbonyl, hydroxycarbonyl, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, $C_{1-6}$alkylaminocarbonyloxy, di($C_{1-6}$)alkylaminocarbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, $C_{1-6}$alkylcarbonyl-N—($C_{1-6}$)alkylamino, arylcarbonyl (where the aryl group is itself optionally substituted with halogen or $C_{1-6}$ alkyl), or two adjacent positions on an aryl or heteroaryl system may be cyclised to form a 4, 5, 6 or 7 membered carbocyclic or heterocyclic ring, itself optionally substituted with halogen or $C_{1-6}$ alkyl. Further substituents for aryl or heteroaryl include arylcarbonylamino (where the aryl group is substituted by $C_{1-6}$ alkyl or halogen), $C_{1-6}$alkoxycarbonylamino, $C_{1-6}$alkoxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$alkylaminocarbonylamino, di($C_{1-6}$)alkylaminocarbonylamino, arylaminocarbonylamino (where the aryl group is substituted by $C_{1-6}$ alkyl or halogen), aryl-N—($C_{1-6}$)alkylaminocarbonylamino (where the aryl group is substituted by $C_{1-6}$ alkyl or halogen), $C_{1-6}$alkylaminocarbonyl-N—($C_{1-6}$)alkylamino, di($C_{1-6}$)alkylaminocarbonyl-N—($C_{1-6}$)alkylamino, arylaminocarbonyl-N—($C_{1-6}$)alkylamino (where the aryl group is substituted by $C_{1-6}$ alkyl or halogen) and aryl-N—($C_{1-6}$)alkylaminocarbonyl-N—($C_{1-6}$)alkylamino (where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, hydroxycaronyl, $C_{1-6}$ alkylcarbonyl, $C_{1-6}$ alkoxycarbonyl, aryl, heteroaryl, $C_{1-6}$ alkylamino, di($C_{1-6}$ alkyl)amino, $C_{1-6}$alkylaminocarbonyl, or di($C_{1-6}$ alkyl)aminocarbonyl.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, N-methylpiperazine, thiomorpholine and morpholine each of which may be substituted by one or two independently selected ($C_{1-6}$) alkyl groups.

Preferably the optional substituents on an alkyl moiety include one or more of halogen, nitro, cyano, hydroxycarbonyl, $C_{1-10}$ alkoxy (itself optionally substituted by $C_{1-10}$ alkoxy), aryl($C_{1-4}$)alkoxy, $C_{1-10}$ alkylthio, $C_{1-10}$ alkylcarbonyl, $C_{3-6}$ cycloalkylcarbonyl, $C_{1-10}$ alkoxycarbonyl, $C_{1-6}$ alkylaminocarbonyl, di-($C_{1-6}$ alkyl)-aminocarbonyl, $C_{1-6}$alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$) alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-3}$ alkyl.

Preferably the optional substituents for cycloalkyl include halogen, cyano and $C_{1-6}$ alkyl.

The optional substituents for cycloalkenyl preferably include $C_{1-3}$ alkyl, halogen and cyano.

In particularly preferred embodiments of the invention, the preferred groups for $R^1$, $R^2$, $R^3$, and Z, in any combination thereof, are set out below.

In preferred embodiments $R^1$ is $C_{1-5}$ alkyl. More preferably $R^1$ is $C_{1-3}$ alkyl, in particular, methyl, ethyl, n-propyl, or iso-propyl. Most preferably $R^1$ is ethyl or n-propyl.

$R^2$ is preferably chloro or bromo. More preferably, $R^2$ is chloro.

In further preferred embodiments, $R^3$ is $C_{2-6}$ alkyl, $C_{1-4}$ haloalkyl, $C_{1-6}$ hydroxyalkyl, $C_{1-6}$ alkoxymethyl, di($C_{1-5}$alkoxy)methyl, $C_{1-6}$ alkylthiomethyl, $C_{1-5}$alkylsulfinylmethyl, bromo, or iodo.

Preferably, in the compounds of the formula (I), $R^3$ is $C_{1-4}$ haloalkyl, bromo, or iodo. More preferably, $R^3$ is fluoromethyl, difluoromethyl, trifluoromethyl, bromo or iodo. Most preferably $R^3$ is fluoromethyl, difluoromethyl, or trifluoromethyl.

In certain embodiments, Z is selected from: hydrogen; cyano; formyl; optionally substituted $C_{1-6}$ alkyl; $C_{3-6}$ alkenyl; $C_{3-6}$ haloalkenyl; $C_{3-6}$ alkinyl; $C_{1-6}$ alkylthio; $C_{1-6}$ haloalkylthio; $C_{1-6}$ cyanoalkylthio; optionally substituted phenylthio, said substitution being selected from halogen, nitro, cyano, $C_{1-3}$ alkyl, and $C_{1-3}$ alkoxy; $C_{1-6}$ alkyldithio; di($C_{1-4}$ alkyl) aminothio; optionally substituted $C_{1-6}$ alkylcarbonyl, said substitution being selected from halogen, cyano, and $C_{1-3}$alkoxy; $C_{2-6}$ alkenylcarbonyl; $C_{3-6}$ cycloalkylcarbonyl; optionally substituted phenylcarbonyl, said substitution being selected from halogen, nitro, cyano, $C_{1-3}$ alkyl, and $C_{1-3}$ alkoxy; optionally substituted heteroarylcarbonyl, said substitution being selected from halogen, nitro, cyano, $C_{1-3}$ alkyl, and $C_{1-3}$ alkoxy; $C_{1-6}$ alkoxycarbonyl; $C_{1-6}$ alkylthio-carbonyl; optionally substituted phenylthio-carbonyl, said substitution being selected from halogen, nitro, cyano, alkyl, and $C_{1-3}$ alkoxy; N,N-di $C_{1-3}$ alkylaminocarbonyl; $C_{1-3}$ alkylaminocarbonyl; $C_{3-5}$ alkenylaminocarbonyl; $C_{3-5}$ alkynylaminocarbonyl; phenylaminocarbonyl wherein said phenyl group is optionally substituted by halogen, nitro, cyano, $C_{1-3}$ alkyl, or $C_{1-3}$ alkoxy); N-phenyl-N-methyl aminocarbonyl wherein said phenyl group is optionally substituted by halogen, nitro, cyano, $C_{1-3}$ alkyl, or $C_{1-3}$ alkoxy); $C_{1-6}$ alkoxythionocarbonyl; $C_{1-6}$ alkylthiothionocarbonyl; phenylthiothionocarbonyl optionally substituted by halogen, nitro, cyano, $C_{1-3}$ alkyl, or $C_{1-3}$ alkoxy; N,N-di $C_{1-3}$ alkylaminothionocarbonyl; $C_{1-3}$ alkylaminothionocarbonyl; phenylaminothionocarbonyl wherein said phenyl group is optionally substituted by halogen, nitro, cyano, $C_{1-3}$ alkyl, or $C_{1-3}$ alkoxy; N-phenyl-N-methyl aminothionocarbonyl wherein said phenyl group is optionally substituted by halogen, nitro, cyano, $C_{1-3}$ alkyl, or $C_{1-3}$ alkoxy; $C_{1-3}$ alkylsulfonyl; $C_{1-3}$ haloalkylsulfonyl; $C_{1-3}$ alkenylsulfonyl; phenylsulfonyl optionally substituted by halogen, nitro, cyano, $C_{1-3}$ alkyl, or $C_{1-3}$ alkoxy; N,N-di $C_{1-3}$ alkylaminosulfonyl; di $C_{1-3}$ alkoxy-P(=O)—; di $C_{1-3}$ alkylthio-P(=O)—; di $C_{1-3}$ alkoxy-P(=S)—; di $C_{1-3}$ alkylthio-P(=S)—; ($C_{1-3}$ alkoxy)(phenyl)P(=O)—; ($C_{1-3}$ alkoxy)(phenyl)P(=S)—; $C_{1-3}$ alkyl-N=CH—; $C_{1-3}$ alkoxy-N=CH—; cyano-N=CH—; phenyl-N=CH— wherein said phenyl group is optionally substituted by halogen, nitro, cyano, $C_{1-3}$ alkyl, or $C_{1-3}$ alkoxy; 2-pyridyl-N=CH—; 3-pyridyl-N=CH—; 2-thiazolyl-N=CH—; or a compound of formula (II) wherein B is S— or $CH_2$—; and wherein when Z is an optionally substituted $C_{1-6}$ alkyl group said substitution is selected from: 1-7 fluorine atoms; 1-3 chlorine atoms; 1-3 bromine atoms; a cyano group; 1-2 $C_{1-3}$alkoxy groups; a $C_{1-3}$ haloalkoxy group; a $C_{1-3}$alkylthio group; a $C_{1-3}$ haloalkylthio group; an allyloxy group; a propargyloxy group; a $C_{3-6}$ cycloalkyl group; a phenyl group, wherein said phenyl group is optionally substituted with halogen, nitro, cyano, $C_{1-3}$ alkyl or $C_{1-3}$ alkoxy; a $C_{1-3}$alkylcarbonyloxy group; a $C_{1-3}$alkoxycarbonyl group; a $C_{1-3}$alkylcarbonyl group; and an optionally substituted benzoyl, said substitution being selected from halogen, nitro, $C_{1-3}$ alkyl, $C_{1-3}$ alkoxy, and a cyano group.

Preferably, Z is selected from: hydrogen; cyano; formyl; $C_{1-3}$ alkyl; $C_{1-3}$ haloalkyl; $C_{1-3}$ cyanoalkyl; $C_{1-3}$ alkoxy-$C_{1-3}$ alkyl; $C_{1-3}$ benzyloxy-$C_{1-3}$ alkyl; allyl; propargyl; $C_{1-6}$ alkylthio; $C_{1-6}$ haloalkylthio; phenylthio optionally substituted with halogen, $C_{1-3}$ alkyl, or $C_{1-3}$ alkoxy; $C_{1-6}$ alkylcarbonyl; phenylcarbonyl optionally substituted by halogen, $C_{1-3}$ alkyl or $C_{1-3}$ alkoxy; $C_{1-6}$ alkoxycarbonyl; $C_{1-3}$ alkylaminocarbonyl; phenylaminocarbonyl wherein said phenyl group is optionally substituted with halogen, $C_{1-3}$ alkyl or $C_{1-3}$ alkoxy; $C_{1-3}$ alkylaminothionocarbonyl; phenylaminothionocarbonyl wherein said phenyl group is optionally substituted by halogen, $C_{1-3}$ alkyl or $C_{1-3}$ alkoxy; $C_{1-3}$ alkylsulfonyl; $C_{1-3}$ haloalkylsulfonyl; di-$C_{1-3}$ alkoxy-P(=O)—; $C_{1-3}$ alkoxy-N=CH—; cyano-N=CH—; and 2-pyridyl-N=CH—. More preferably Z is selected from the substituents given for Z in Table 2. More preferably still Z is either hydrogen or C(O)Ot-butyl. Most preferably Z is hydrogen.

In the most preferred embodiments $R^1$ is ethyl or n-propyl, and Z is hydrogen.

The compounds described below are illustrative of novel compounds of the invention.

Table 1 provides 30 compounds of formula Ia

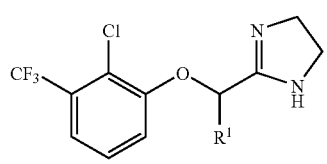
(Ia)

wherein the values of $R^1$ are given in table 1.

TABLE 1

| Compound No | $R^1$ |
| --- | --- |
| I-1 | $CH_3$ |
| I-2 | $CH_2CH_3$ |
| I-3 | $CH_2CH_2CH_3$ |
| I-4 | $CH(CH_3)_2$ |
| I-5 | $CH_2CH_2CH_2CH_3$ |
| I-6 | $CH(CH_3)CH_2CH_3$ |
| I-7 | $CH_2CH(CH_3)_2$ |
| I-8 | $C(CH_3)_3$ |
| I-9 | $CH_2CH_2CH_2CH_2CH_3$ |
| I-10 | $CH(CH_3)CH_2CH_2CH_3$ |
| I-11 | $CH_2CH(CH_3)CH_2CH_3$ |
| I-12 | $CH_2CH_2CH(CH_3)_2$ |
| I-13 | $C(CH_3)_2CH_2CH_3$ |
| I-14 | $CH(CH_2CH_3)_2$ |
| I-15 | $CH(CH_3)CH(CH_3)_2$ |
| I-16 | $CH_2CH_2CH_2CH_2CH_2CH_3$ |
| I-17 | $CH_2CH(CH_3)CH_2CH_2CH_3$ |
| I-18 | $CH_2CH_2CH(CH_2CH_3)CH_2CH_3$ |
| I-19 | $CH_2CH_2CH_2CH(CH_2CH_3)_2$ |
| I-20 | $CH_2C(CH_3)_2CH_2CH_3$ |
| I-21 | $CH_2CH(CH_2CH_3)_2$ |
| I-22 | $CH_2CH(CH_2CH_3)CH(CH_3)_2$ |
| I-23 | $CH(CH_3)CH_2CH_2CH_2CH_3$ |
| I-24 | $CH_2CH_2CH(CH_3)CH_2CH_3$ |
| I-25 | $CH_2CH_2CH_2CH(CH_3)_2$ |
| I-26 | $C(CH_3)_2CH_2CH_2CH_3$ |
| I-27 | $CH_2CH(CH_2CH_3)_2$ |
| I-28 | $CH_2CH(CH_3)CH(CH_3)_2$ |
| I-29 | $CH_2CH_2CH_2CH_2CH_2CH_2CH_3$ |
| I-30 | $CH_2CH_2CH_2CH_2CH_2CH_2CH_2CH_3$ |

30 Compounds of formula Ib

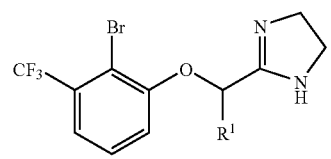
(Ib)

wherein the values of $R^1$ are as given in Table 1 for compounds I-1 to I-30, are designated as compound Nos. II-1 to II-30, respectively.

30 Compounds of formula Ic

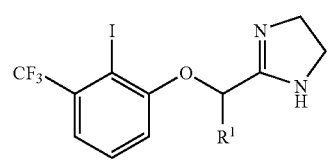
(Ic)

wherein the values of $R^1$ are as given in Table 1 for compounds I-1 to I-30, are designated as compound Nos. III-1 to III-30, respectively.

30 Compounds of formula Id

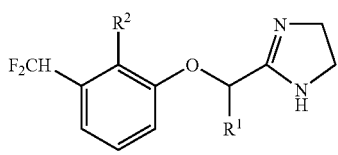

(Id)

wherein the values of R[1] are as given in Table 1 for compounds I-1 to I-30, are designated as compound Nos. IV-1 to IV-30, respectively.

30 Compounds of formula Ie

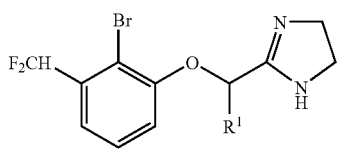

(Ie)

wherein the values of R[1] are as given in Table 1 for compounds I-1 to I-30, are designated as compound Nos. V-1 to V-30, respectively.

30 Compounds of Formula If

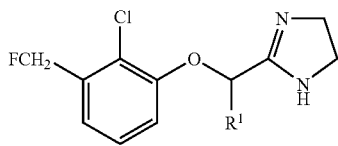

(If)

wherein the values of R[1] are as given in Table 1 for compounds I-1 to I-30, are designated as compound Nos. VI-1 to VI-30, respectively.

Table 2 provides 194 compounds of formula Ip

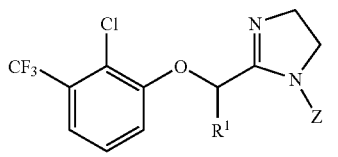

(Ip)

wherein the values of R[1] and Z are given in Table 2 below.

TABLE 2

| Compound No | R[1] | Z |
|---|---|---|
| XV-1 | Et | —CN |
| XV-2 | Et | —NO$_2$ |
| XV-3 | Et | Me |
| XV-4 | Et | Et |
| XV-5 | Et | Pr |
| XV-6 | Et | Bu |
| XV-7 | Et | allyl |
| XV-8 | Et | isopropenyl |
| XV-9 | Et | vinyl |
| XV-10 | Et | but-2-en1-yl |
| XV-11 | Et | propargyl |

TABLE 2-continued

| Compound No | R[1] | Z |
|---|---|---|
| XV-12 | Et | but-1-en-1-yl |
| XV-13 | Et | but-3-en1-yl |
| XV-14 | Et | but-1-en2-yl |
| XV-15 | Et | but-2-en2-yl |
| XV-16 | Et | but-3-en2-yl |
| XV-17 | Et | methoxymethyl |
| XV-18 | Et | ethoxymethyl |
| XV-19 | Et | propoxymethyl |
| XV-20 | Et | benzyloxymethyl |
| XV-21 | Et | 1-methoxyethyl |
| XV-22 | Et | 2-methoxyethyl |
| XV-23 | Et | —CH$_2$OCOMe |
| XV-24 | Et | —CH$_2$OCOEt |
| XV-25 | Et | —CH$_2$OCOiPr |
| XV-26 | Et | —CH$_2$OCOtBu |
| XV-27 | Et | —CH$_2$OCOPh |
| XV-28 | Et | —CH$_2$OCOEt |
| XV-29 | Et | —CH=N—OMe |
| XV-30 | Et | —CH=N—OEt |
| XV-31 | Et | —CH=N-Me |
| XV-32 | Et | —CH=N-Et |
| XV-33 | Et | —CH=N-Ph |
| XV-34 | Et | —CH=N-(2-pyridyl) |
| XV-35 | Et | —CH=N—C≡N |
| XV-36 | Et | —P(O)(OEt)$_2$ |
| XV-37 | Et | —P(S)(OEt)$_2$ |
| XV-38 | Et | —P(O)(OMe)$_2$ |
| XV-39 | Et | —P(S)(OMe)$_2$ |
| XV-40 | Et | —P(O)(OPh)$_2$ |
| XV-41 | Et | —P(S)(OPh)$_2$ |
| XV-42 | Et | —P(O)(OBn)$_2$ |
| XV-43 | Et | —P(S)(OBn)$_2$ |
| XV-44 | Et | —P(O)(NMe$_2$)$_2$ |
| XV-45 | Et | —P(S)(NMe$_2$)$_2$ |
| XV-46 | Et | —P(O)(NEt$_2$)$_2$ |
| XV-47 | Et | —P(S)(NEt$_2$)$_2$ |
| XV-48 | Et | —OH |
| XV-49 | Et | —OMe |
| XV-50 | Et | —OAc |
| XV-51 | Et | —OBz |
| XV-52 | Et | SMe |
| XV-53 | Et | SCl$_3$ |
| XV-54 | Et | SPh |
| XV-55 | Et | S(O)Ph |
| XV-56 | Et | S(O)$_2$Me |
| XV-57 | Et | S(O)$_2$CF$_3$ |
| XV-58 | Et | S(O)$_2$Ph |
| XV-59 | Et | C(O)Me |
| XV-60 | Et | C(O)Et |
| XV-61 | Et | C(O)iPr |
| XV-62 | Et | C(O)tBu |
| XV-63 | Et | C(O)CH$_2$OMe |
| XV-64 | Et | C(O)CH$_2$Cl |
| XV-65 | Et | C(O)CHCl$_2$ |
| XV-66 | Et | C(O)CCl$_3$ |
| XV-67 | Et | C(O)Ph |
| XV-68 | Et | C(O)(4-fluorophenyl) |
| XV-69 | Et | C(O)(4-chlorophenyl) |
| XV-70 | Et | C(O)(4-methoxyphenyl) |
| XV-71 | Et | C(O)(2,4-dichlorophenyl) |
| XV-72 | Et | C(O)(2,6-dichlorophenyl) |
| XV-73 | Et | C(O)(2,6-difluorophenyl) |
| XV-74 | Et | C(O)OMe |
| XV-75 | Et | C(O)OEt |
| XV-76 | Et | C(O)OiPr |
| XV-77 | Et | C(O)OtBu |
| XV-78 | Et | C(O)OPh |
| XV-79 | Et | C(O)O(4-fluorophenyl) |
| XV-80 | Et | C(O)O(4-chlorophenyl) |
| XV-81 | Et | C(O)O(4-methoxyphenyl) |
| XV-82 | Et | C(O)O(2,4-dichlorophenyl) |
| XV-83 | Et | C(O)O(2,6-dichlorophenyl) |
| XV-84 | Et | C(O)O(2,6-difluorophenyl) |
| XV-85 | Et | C(O)NHMe |
| XV-86 | Et | C(O)NMe$_2$ |
| XV-87 | Et | C(O)NHEt |
| XV-88 | Et | C(O)NEt$_2$ |
| XV-89 | Et | C(O)NHiPr |

TABLE 2-continued

| Compound No | R¹ | Z |
|---|---|---|
| XV-90 | Et | C(O)NHtBu |
| XV-91 | Et | C(O)NHPh |
| XV-92 | Et | C(O)NH(4-fluorophenyl) |
| XV-93 | Et | C(O)NH(4-chlorophenyl) |
| XV-94 | Et | C(O)NH(4-methoxyphenyl) |
| XV-95 | Et | C(O)NH(2,4-dichlorophenyl) |
| XV-96 | Et | C(O)NH(2,6-dichlorophenyl) |
| XV-97 | Et | C(O)NH(2,6-difluorophenyl) |
| XV-98 | nPr | —CN |
| XV-99 | nPr | —NO₂ |
| XV-100 | nPr | Me |
| XV-101 | nPr | Et |
| XV-102 | nPr | Pr |
| XV-103 | nPr | Bu |
| XV-104 | nPr | allyl |
| XV-105 | nPr | isopropenyl |
| XV-106 | nPr | vinyl |
| XV-107 | nPr | propargyl |
| XV-108 | nPr | but-2-en1-yl |
| XV-109 | nPr | but-1-en-1-yl |
| XV-110 | nPr | but-3-en1-yl |
| XV-111 | nPr | but-1-en2-yl |
| XV-112 | nPr | but-2-en2-yl |
| XV-113 | nPr | but-3-en2-yl |
| XV-114 | nPr | methoxymethyl |
| XV-115 | nPr | ethoxymethyl |
| XV-116 | nPr | propoxymethyl |
| XV-117 | nPr | benzyloxymethyl |
| XV-118 | nPr | 1-methoxyethyl |
| XV-119 | nPr | 2-methoxyethyl |
| XV-120 | nPr | —CH₂OCOMe |
| XV-121 | nPr | —CH₂OCOEt |
| XV-122 | nPr | —CH₂OCOiPr |
| XV-123 | nPr | —CH₂OCOtBu |
| XV-124 | nPr | —CH₂OCOPh |
| XV-125 | nPr | —CH₂OCOEt |
| XV-126 | nPr | —CH=N—OMe |
| XV-127 | nPr | —CH=N—OEt |
| XV-128 | nPr | —CH=N-Me |
| XV-129 | nPr | —CH=N-Et |
| XV-130 | nPr | —CH=N-Ph |
| XV-131 | nPr | —CH=N-(2-pyridyl) |
| XV-132 | nPr | —CH=N—C≡N |
| XV-133 | nPr | —P(O)(OEt)₂ |
| XV-134 | nPr | —P(S)(OEt)₂ |
| XV-135 | nPr | —P(O)(OMe)₂ |
| XV-136 | nPr | —P(S)(OMe)₂ |
| XV-137 | nPr | —P(O)(OPh)₂ |
| XV-138 | nPr | —P(S)(OPh)₂ |
| XV-139 | nPr | —P(O)(OBn)₂ |
| XV-140 | nPr | —P(S)(OBn)₂ |
| XV-141 | nPr | —P(O)(NMe₂)₂ |
| XV-142 | nPr | —P(S)(NMe₂)₂ |
| XV-143 | nPr | —P(O)(NEt₂)₂ |
| XV-144 | nPr | —P(S)(NEt₂)₂ |
| XV-145 | nPr | —OH |
| XV-146 | nPr | —OMe |
| XV-147 | nPr | —OAc |
| XV-148 | nPr | —OBz |
| XV-149 | nPr | SMe |
| XV-150 | nPr | SCCl₃ |
| XV-151 | nPr | SPh |
| XV-152 | nPr | S(O)Ph |
| XV-153 | nPr | S(O)₂Me |
| XV-154 | nPr | S(O)₂CF₃ |
| XV-155 | nPr | S(O)₂Ph |
| XV-156 | nPr | C(O)Me |
| XV-157 | nPr | C(O)Et |
| XV-158 | nPr | C(O)iPr |
| XV-159 | nPr | C(O)tBu |
| XV-160 | nPr | C(O)CH₂OMe |
| XV-161 | nPr | C(O)CH₂Cl |
| XV-162 | nPr | C(O)CHCl₂ |
| XV-163 | nPr | C(O)CCl₃ |
| XV-164 | nPr | C(O)Ph |
| XV-165 | nPr | C(O)(4-fluorophenyl) |
| XV-166 | nPr | C(O)(4-chlorophenyl) |
| XV-167 | nPr | C(O)(4-methoxyphenyl) |
| XV-168 | nPr | C(O)(2,4-dichlorophenyl) |
| XV-169 | nPr | C(O)(2,6-dichlorophenyl) |
| XV-170 | nPr | C(O)(2,6-difluorophenyl) |
| XV-171 | nPr | C(O)OMe |
| XV-172 | nPr | C(O)OEt |
| XV-173 | nPr | C(O)OiPr |
| XV-174 | nPr | C(O)OtBu |
| XV-175 | nPr | C(O)OPh |
| XV-176 | nPr | C(O)O(4-fluorophenyl) |
| XV-177 | nPr | C(O)O(4-chlorophenyl) |
| XV-178 | nPr | C(O)O(4-methoxyphenyl) |
| XV-179 | nPr | C(O)O(2,4-dichlorophenyl) |
| XV-180 | nPr | C(O)O(2,6-dichlorophenyl) |
| XV-181 | nPr | C(O)O(2,6-difluorophenyl) |
| XV-182 | nPr | C(O)NHMe |
| XV-183 | nPr | C(O)NMe₂ |
| XV-184 | nPr | C(O)NHEt |
| XV-185 | nPr | C(O)NEt₂ |
| XV-186 | nPr | C(O)NHiPr |
| XV-187 | nPr | C(O)NHtBu |
| XV-188 | nPr | C(O)NHPh |
| XV-189 | nPr | C(O)NH(4-fluorophenyl) |
| XV-190 | nPr | C(O)NH(4-chlorophenyl) |
| XV-191 | nPr | C(O)NH(4-methoxyphenyl) |
| XV-192 | nPr | C(O)NH(2,4-dichlorophenyl) |
| XV-193 | nPr | C(O)NH(2,6-dichlorophenyl) |
| XV-194 | nPr | C(O)NH(2,6-difluorophenyl) |

194 Compounds of Formula Iq

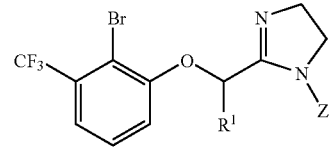

(Iq)

wherein the values of R¹ and Z are as given in Table 2 for compounds XV-1 to XV-194, are designated as compound Nos. XVI-1 to XVI-194, respectively.

194 Compounds of Formula Ir

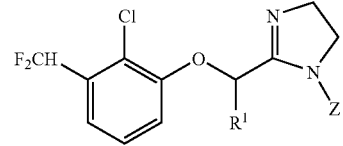

(Ir)

wherein the values of R¹ and Z are as given in Table 2 for compounds XV-1 to XV-194, are designated as compound Nos. XVII-1 to XVII-194, respectively.

194 Compounds of Formula Is

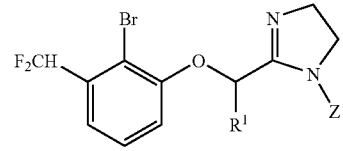

(Is)

wherein the values of R¹ and Z are as given in Table 2 for compounds XV-1 to XV-194, are designated as compound Nos. XVIII-1 to XVIII-194, respectively.

194 Compounds of Formula It

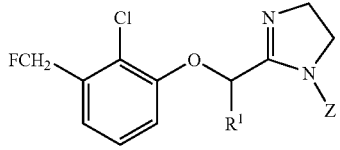

(It)

wherein the values of $R^1$ and Z are as given in Table 2 for compounds XV-1 to XV-194, are designated as compound Nos. XIX-1 to XIX-194, respectively.

Table 3 below provides characterising data for some of the compounds described above; other compounds are only described in this table.

TABLE 3

Characterising data for compounds of the invention (I)

| Comp. no | $R^1$ | $R^2$ | $R^3$ | Z | m.p. [° C.] *) |
|---|---|---|---|---|---|
| 1.001 | CH$_2$CH$_3$ | Cl | CF$_3$ | H | 102-103 |
| 1.002 | CH$_2$CH$_3$ | Cl | CHF$_2$ | H | 96-97 |
| 1.003 | CH$_2$CH$_3$ | Cl | CHF$_2$ | C(O)OtBu | Gum |
| 1.004 | CH$_2$CH$_3$ | Cl | C(O)H | C(O)OtBu | Oil |
| 1.005 | CH$_2$CH$_3$ | Cl | CH$_2$OH | H | 116-120 |
| 1.006 | CH$_2$CH$_3$ | Cl | CH$_2$F | H | 97-99 |
| 1.007 | CH$_2$CH$_3$ | Cl | CH$_2$OH | C(O)OtBu | 108-109 |
| 1.008 | CH$_2$CH$_3$ | Cl | CH$_2$OCH$_3$ | H | 99-100 |
| 1.009 | CH$_2$CH$_3$ | Cl | CH$_2$OC$_2$H$_5$ | H | 112-113 |
| 1.010 | CH$_2$CH$_3$ | Cl | CH(OCH$_3$)$_2$ | H | Gum |
| 1.011 | CH$_2$CH$_3$ | Cl | ethinyl | H | Solid |
| 1.012 | CH$_2$CH$_3$ | Cl | Vinyl | H | Solid |
| 1.013 | n-propyl | Cl | C≡CPh | H | 99-104 |
| 1.014 | CH$_3$ | Cl | CF$_3$ | H | 96-98 |
| 1.015 | n-propyl | Cl | CF$_3$ | H | 111-113 |
| 1.016 | i-propyl | Cl | CF$_3$ | H | 84-86 |
| 1.017 | CH$_2$CH$_3$ | Cl | Vinyl | C(O)OtBu | Gum |
| 1.018 | CH$_2$CH$_3$ | Cl | CH$_2$Cl | H | Gum |
| 1.019 | CH$_2$CH$_3$ | Cl | CH$_2$SCH$_3$ | H | Gum |
| 1.020[a)] | CH$_2$CH$_3$ | I | CF$_3$ | H | 119-132 |
| 1.021 | n-propyl | Br | Br | H | 130-132 |
| 1.022 | n-propyl | Br | I | H | 120-122 |
| 1.023 | CH$_3$ | Cl | CHF$_2$ | H | 105-108 |
| 1.024 | CH$_2$CH$_3$ | Cl | CN | H | 115-117 |
| 1.025 | CH$_2$CH$_3$ | Cl | CN | C(O)OtBu | 80-81 |
| 1.026[b)] | n-propyl | Cl | CF$_3$ | H | 164-167 |
| 1.027 | n-butyl | Cl | CF$_3$ | H | 73-75 |
| 1.028 | n-propyl | Cl | CHF$_2$ | H | 137-139 |
| 1.029 | n-butyl | Cl | CHF$_2$ | H | 96-98 |
| 1.030 | i-propyl | Cl | CHF$_2$ | H | 95-97 |
| 1.031 | n-propyl | Cl | CH$_2$F | H | 128-130 |
| 1.032 | nBu | Cl | CH$_2$F | H | 101-103 |
| 1.033 | n-propyl | Cl | I | H | 111-117 |
| 1.034 | CH$_2$CH$_3$ | Cl | CH$_2$Cl | C(O)OtBu | 81-85 |
| 1.035 | CH$_2$CH$_3$ | Cl | CH$_2$S(O)CH$_3$ | H | 140-141 |
| 1.036 | n-propyl | Cl | Br | H | 138-140 |
| 1.037 | i-propyl | Cl | CH$_2$F | H | 88-92 |

[a)] maleate salt
[b)] HCl salt

*) $^1$H-NMR (CDCl$_3$) of selected compounds:
1.010   7.25, d, 1H; 7.20, t, 1H; 7.07, d, 1H; 5.64, s, 1H; 4.89, t, 1H; 3.67, m, 2H; 3.53, m, 2H; 3.40, s, 3H; 3.38, s, 3H; 2.02, m, 2H; 0.98, t, 3H.
1.015   7.36, t, 1H; 7.31, d, 1H; 7.11, d, 1H; 4.90, d, 1H; 3.14, m, 4H; 2.60, m, 1H; 1.18, d, 3H; 1.10, d, 3H.

Compounds of the invention can be prepared by a variety of methods, for example those described below.

Compounds of the formula I in which Z is not H can be prepared from compounds of the formula I in which Z is H, by treatment with the appropriate reagent. Depending on the nature of Z this can be for example an alkylating agent, an acylating agent, a carbamoylating agent, a phosphorylating agent, a sulfenylating agent or an oxidising agent. These derivatisating agents are generally electrophiles. Methods for the conversion of NH groups into NZ groups can be found for example in T. W. Greene and P. G. M. Wuts "Protecting Groups in Organic Synthesis" 3$^{rd}$ Edition, Wiley, NY 1999.

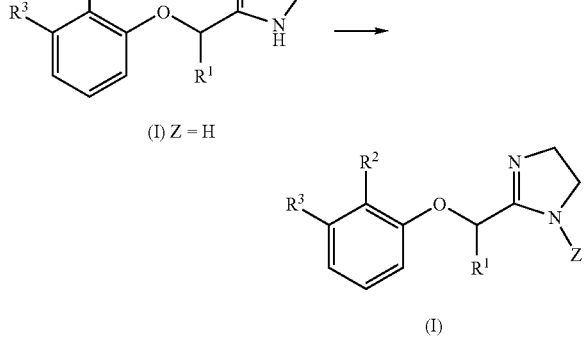

Compounds of the formula I can be prepared by alkylation of a phenol of the formula 2, with a 2-haloalkylimidazoline of the formula 3 (J. Am. Chem. Soc. 1947, 69, 1688).

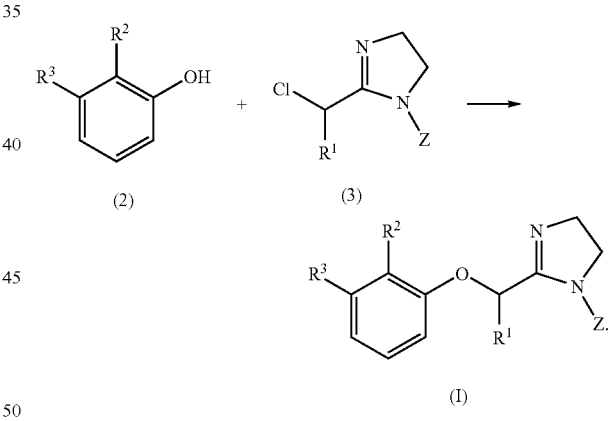

Compounds of the formula I can be prepared from nitriles of the formula 4, by treatment with a diamine of the formula 5, wherein Z has the meanings assigned to it above. This is advantageously performed in the presence of a catalyst such as CS$_2$, P$_2$S$_5$ (J. of Med. Chem., 2003 46, 1962) or Na$_2$S$_4$ (DE 2512513). The nitrile 4 can be converted to imidates of the formula 6 using an alcohol such as methanol and a catalytic amount of base such as NaOH, or to salts of imidate of formula 6a using an alcohol such as methanol or ethanol and an acid such as HCl. Imidates of the formula 6 and/or formula 6a can be converted to compounds of the formula I on treatment with diamines of the formula 5 (J. of Med. Chem., 2004, 47, 6160; J. Am. Chem. Soc. 1947, 69, 1688). Nitriles of the formula 4 can be prepared by alkylating phenols of the formula 2 with a nitrile of the formula 8, bearing a leaving group L$_1$ (J. Am. Chem. Soc. 1947, 69, 1688).

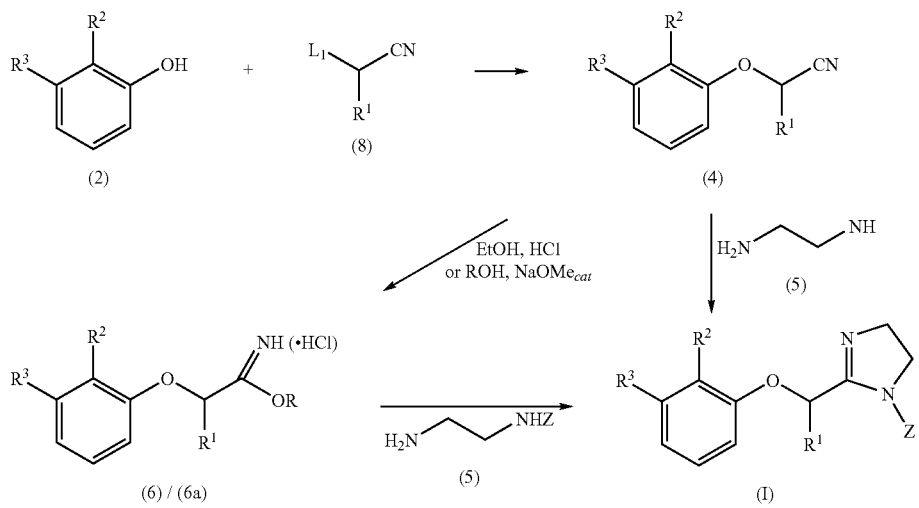

In a special variant anilines of formula 2a can be reacted with nitriles of formula 8 to form compounds of the formula 4a. The amines of formula 4a can be converted then to nitriles of formula 4, in which $R^2$ is chloro, bromo or iodo by conversion to its corresponding diazonium salt and further conversion to the corresponding halide (H. Zollinger, "Diazo Chemistry 1, Aromatic and heteroaromatic compounds" VCH, Weinheim, 1994).

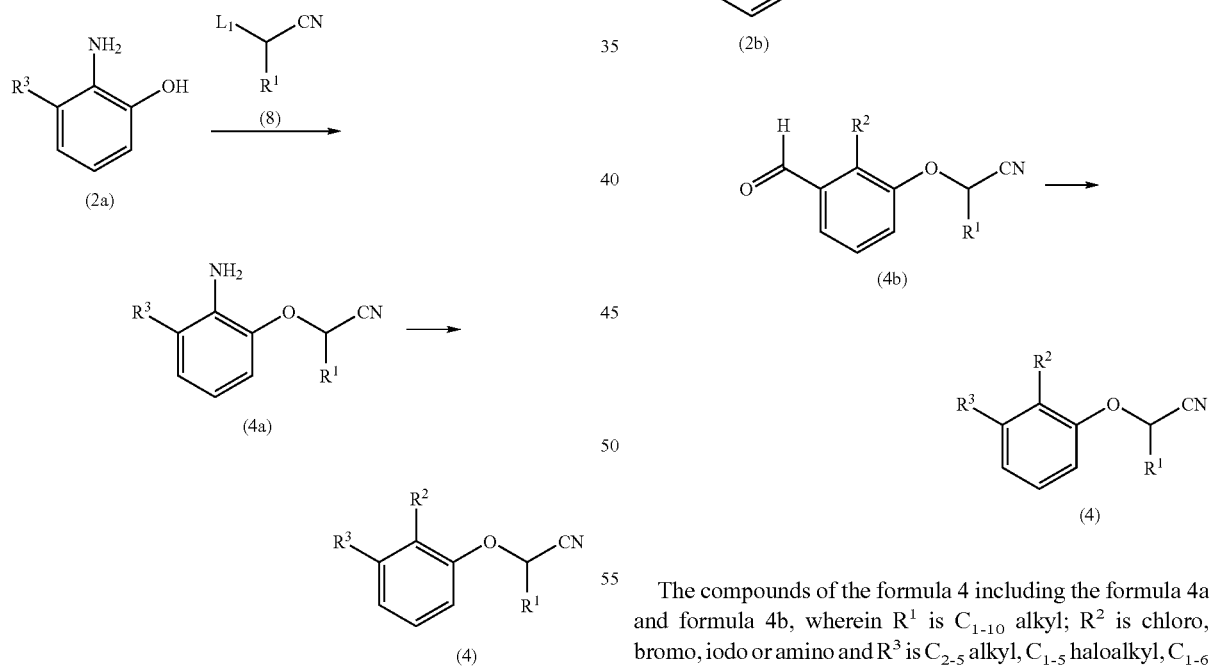

In another special variant aldehydes of formula 2b can be reacted with nitriles of formula 8 to get compounds of the formula 4b. The aldehydes of formula 4b can be converted then to the corresponding compounds of formula 4, in which $R^3$ is $C_{2-5}$ alkyl, $C_{1-4}$ haloalkyl, $C_{1-6}$ hydroxyalkyl, $C_{1-5}$ alkoxy-($C''$)-alkyl, di-($C_{1-5}$ alkoxy)-($C_{1-3}$)-alkyl, $C_{1-5}$ alkylthio-($C_{1-3}$)-alkyl, $C_{2-5}$ alkenyl, $C_{1-5}$ haloalkenyl, $C_{2-5}$ alkinyl, $C_{3-6}$ cycloalkyl, $C_{3-6}$ cycloalkenyl, hydroxy, $C_{1-5}$ alkoxy, $C_{1-5}$ haloalkoxy, $C_{1-5}$ alkylthio, $C_{1-5}$ haloalkylthio, cyano, or amino by well-known functional group conversions.

The compounds of the formula 4 including the formula 4a and formula 4b, wherein $R^1$ is $C_{1-10}$ alkyl; $R^2$ is chloro, bromo, iodo or amino and $R^3$ is $C_{2-5}$ alkyl, $C_{1-5}$ haloalkyl, $C_{1-6}$ hydroxyalkyl, $C_{1-5}$ alkoxy-($C_{1-3}$)-alkyl, di-($C_{1-5}$ alkoxy)-($C_{1-3}$)-alkyl, $C_{1-5}$ alkylthio-($C_{1-3}$)-alkyl; $C_{1-5}$ alkylsulfinyl-($C_{1-3}$)-alkyl; $C_{2-5}$ alkenyl, $C_{1-5}$ haloalkenyl, $C_{2-5}$ alkinyl, $C_{3-6}$ cycloalkyl, $C_{3-6}$ cycloalkenyl, hydroxy, $C_{1-5}$ alkoxy, haloalkoxy, $C_{1-5}$ alkylthio, $C_{1-5}$ haloalkylthio, formyl, cyano, bromo, or iodo have been specifically designed as intermediates for the synthesis of the compounds of the formula I and are part of this invention.

TABLE 4

Characterising data for compounds of the invention

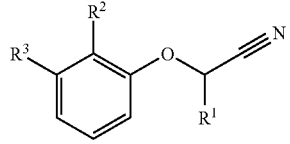

(4)

| Compound No. | $R^1$ | $R^2$ | $R^3$ | Physical data | Remarks *) |
|---|---|---|---|---|---|
| 4.001 | $CH_2CH_3$ | Cl | $CF_3$ | Oil | Ex. 1 |
| 4.002 | $CH_2CH_3$ | Cl | $CHF_2$ | Oil | Ex. 2 |
| 4.003 | $CH_2CH_3$ | Cl | C(O)H | Oil | Ex. 2 |
| 4.004 | $CH_2CH_3$ | Cl | $CH_2OH$ | Oil | |
| 4.005 | $CH_2CH_3$ | Cl | $CH_2F$ | Oil | |
| 4.006 | $CH_2CH_3$ | Cl | $CH_2OCH_3$ | Oil | |
| 4.007 | $CH_2CH_3$ | Cl | $CH_2OC_2H_5$ | Oil | |
| 4.008 | $CH_2CH_3$ | Cl | $CH(OCH_3)_2$ | Oil | |
| 4.009 | $CH(CH_3)_2$ | Cl | $CF_3$ | Oil | |
| 4.010 | $CH_3$ | Cl | $CF_3$ | Oil | |
| 4.011 | n-propyl | Cl | $CF_3$ | Oil | |
| 4.012 | $CH(CH_3)_2$ | Cl | C(O)H | Oil | |
| 4.013 | $CH_3$ | Cl | C(O)H | Oil | |
| 4.014 | n-butyl | Cl | C(O)H | Oil | |
| 4.015 | n-propyl | Cl | C(O)H | Oil | |
| 4.016 | $CH_2CH_3$ | Cl | $CH_2Cl$ | Oil | |
| 4.017 | $CH(CH_3)_2$ | Cl | $CHF_2$ | Oil | |
| 4.018 | $CH_3$ | Cl | $CHF_2$ | Oil | |
| 4.019 | n-butyl | Cl | $CHF_2$ | Oil | |
| 4.020 | n-propyl | Cl | $CHF_2$ | Oil | |
| 4.021 | $CH_2CH_3$ | Cl | $CH_2F$ | Oil | |
| 4.022 | n-butyl | Cl | $CH_2F$ | Oil | |
| 4.023 | n-propyl | Cl | $CH_2F$ | Oil | |
| 4.024 | $CH(CH_3)_2$ | Cl | $CH_2OH$ | Oil | |
| 4.025 | n-butyl | Cl | $CH_2OH$ | Oil | |
| 4.026 | n-propyl | Cl | $CH_2OH$ | Oil | |
| 4.027 | n-propyl | Cl | I | Oil | |
| 4.028 | $CH_2CH_3$ | Cl | CHMe(OH) | Oil | |
| 4.029 | $CH_2CH_3$ | Cl | CHMeF | Oil | |

TABLE 4-continued

Characterising data for compounds of the invention

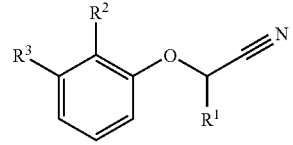

(4)

| Compound No. | $R^1$ | $R^2$ | $R^3$ | Physical data | Remarks *) |
|---|---|---|---|---|---|
| 4.030 | $CH_2CH_3$ | Cl | $CH_2S(O)Me$ | Oil | |
| 4.031 | $CH_2CH_3$ | Cl | $CH_2SMe$ | Oil | |
| 4.032 | $CH_2CH_3$ | Cl | vinyl | Oil | |
| 4.033 | $CH_2CH_3$ | I | $CF_3$ | Oil | |

*) $^1$H-NMR (CDCl$_3$) of selected compounds:
4.009   7.48, d, 1H; 7.40, t, 1H; 7.24, d, 1H; 4.63, d, 1H;
        2.43, m, 1H; 1.28, d, 3H; 1.24, d, 3H.
4.010   7.35 to 7.45, m 3H; 4.40, q, 1H; 1.88, d, 3H.
4.011   7.30 to 7.45, m 3H; 4.81, t, 1H; 2.15, m, 2H; 1.70, d,
        2H; 1.05, t, 3H.

Otherwise esters of the formula 7 can be converted to imidazolines of the formula I by treatment with diamines of the formula 5 (J. Am. Chem. Soc. 1950, 72, 4443-5). Alkylaluminium reagents can be used with advantage to facilitate this reaction. This conversion occurs in two steps by forming first the monoamide 10, which can serve as a precursor to imidazolines of the formula I. Esters of the formula 7 can be prepared by alkylation of phenols of the formula 2 with esters of the formula 9, wherein $L_2$ is a leaving group, and R' is an optionally substituted alkyl, aryl or arylakyl group (typically $C_1$-$C_6$ alkyl, phenyl or benzyl).

The leaving groups $L_1$ and $L_2$ are typically those used for $S_N2$ reactions. $L_1$ and $L_2$ become anions of organic or inorganic acids on leaving their substrates 8 and 9. Typical leaving groups are for example halide like chlorine or bromine, alkylsulfonates like mesylate, and arylsulfonates like p-tosylate.

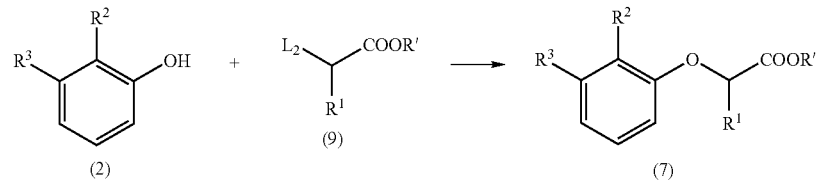

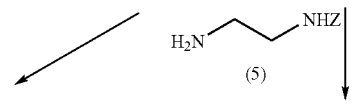

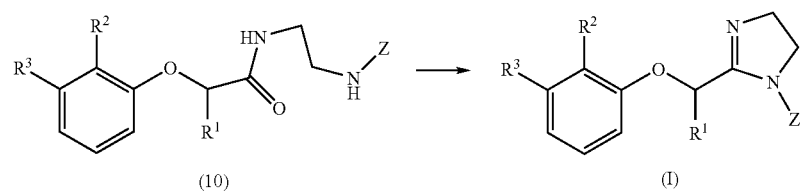

Compounds of the formula I can be prepared from imidazolines of the formula (11) by introduction of a group R¹. This can be done by treating 11 with a base and then subsequently with an electrophile capable of introducing the group R¹. A typical electrophile could be a halide such as R¹—Cl, R¹—Br, or R¹—I. A typical base could be n-butyllithium or mesityl-lithium. The Z group can be a protecting group such tBuOC(O) or (CH₃)₃Si, which can be removed if desired, and a different Z group can be attached as described above if so desired. Compounds of the formula 11 are new, and form yet a further aspect of the invention.

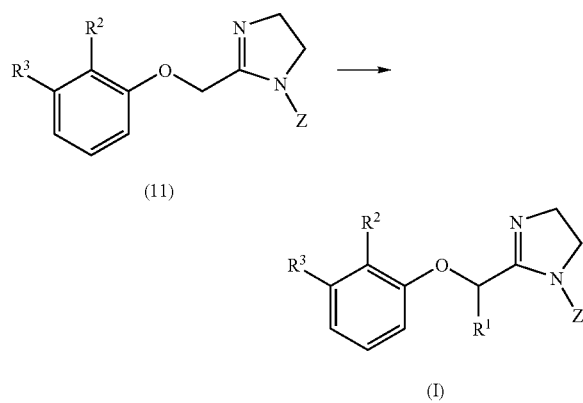

Compounds of formula (2), (2a), (3), (5), (8) and (9) are known compounds or may be obtained readily from known compounds using processes that are routine in the art and with which the skilled man will be familiar.

In a further aspect of the invention the compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarid, nematode and mollusc pests. Insects, acarids, nematodes and molluscs are hereinafter collectively referred to as pests.

By the terms "combat" or "combating" it is meant that compounds of formula (I) may be used to prevent or inhibit infestation by a pest of a crop or locus of a crop. Levels of infestation may be measured by any appropriate method known in the art. An inhibition of infestation is observed where the level of infestation is lower in a crop/locus of a crop treated with a compound of formula (I) in comparison to the level of infestation observed or predicted in a crop/locus of a crop that has not been treated with a compound of formula (I).

By the terms "control" or "controlling" it is meant that, pests are repelled, are unable to feed, are unable to reproduce, and/or are killed. Thus the method of the invention may involve the use of an amount of the active ingredient that is sufficient to repel said pests (i.e a repellently effective amount of active ingredient), an amount of the active ingredient that is sufficient to stop pests feeding, an amount of the active ingredient that is sufficient to inhibit reproduction (e.g. by inhibiting oviposition or ovulation, or by mediating an ovicidal effect), or it may involve the use of an insecticidally-, nematocidally- or molluscidally-effective amount of active ingredient (i.e. an amount sufficient to kill said pests), or the method of the invention may involve any combination of the above effects.

The pests which may be combated and controlled by the use of the invention compounds include those pests associated with agriculture (which term includes the growing of crops for food, fuel and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), and *Deroceras reticulatum* (slug).

The invention therefore provides a method of combating and controlling insects, acarids, or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest. The compounds of formula (I) are preferably used against insects or acarids.

The term "plant" as used herein includes seeds, seedlings, bushes and trees.

In particularly preferred embodiments, compounds of formula (I) and compositions containing such compounds are used in methods of controlling and combating insects in the orders Hemiptera, Lepidoptera, Coleoptera, Thysanoptera, Diptera, Blattodea, Isoptera, Siphonaptera, Hymenoptera, and/or Orthoptera. In certain embodiments, such compounds and compositions are particularly useful in controlling and combating Hemiptera, Lepidoptera, Coleoptera, Thysanoptera, or Diptera. In further embodiments such compounds and compositions are particularly useful in controlling and combating Lepidoptera, Thysanoptera, Isoptera, Siphonaptera, Hymenoptera, or Orthoptera. It is particularly preferred that compounds of formula (I), and compositions containing these compounds are used against Hemipteran insects.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). Suitable inert diluents or carriers are described herein, for example with respect to certain formulation types, and thus the term includes solid diluents, inorganic water soluble salts, water-soluble organic solids and the like as well as simple diluents such as, for example, water and/or oils. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). Such compositions are preferably used against insects, acarids or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water. In particularly preferred embodiments, compounds of formula I will be formulated as an EC or EW formulation:

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or q) Pymetrozine, in particular pymetrozine dihydrate;

r) Tetronic acids such as spirotetramat, spirodiclofen, spiromesifen;

s) Spinosyns, such as spinosad; or t) Anthranilic diamides, such as flubendiamide, Cyazypyr™ or Rynaxypyr™

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoro-methyl-benzimidazole-1-sulphonamide, α-[N-(3-chloro-2,6-xylyl)-2-methoxy-acetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)-propionamide (AC382042), N-(2-methoxy-5-pyridyl)-cyclo-propane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-iso-propyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

Various aspects and embodiments of the present invention will now be illustrated in more detail by way of example. It will be appreciated that modification of detail may be made with out departing from the scope of the invention.

For the avoidance of doubt, where a literary reference, patent application, or patent, is cited within the text of this application, the entire text of said citation is herein incorporated by reference.

EXAMPLES

Example 1

2-[1-(2-Chloro-3-trifluormethyl-phenoxy)-propyl]-4,5-dihydro-1H-imidazole

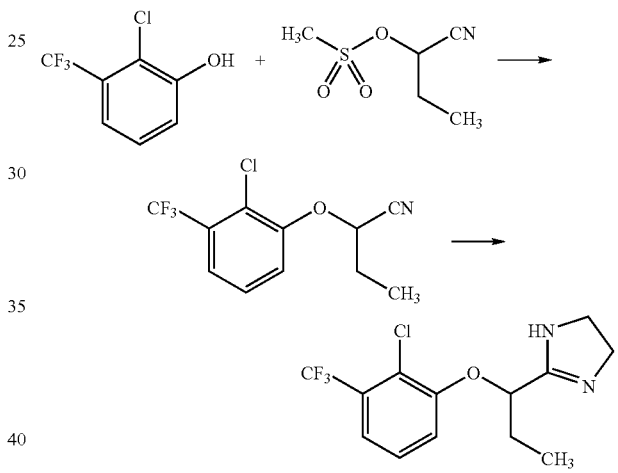

A mixture of 2-(methanesulfonyloxy)-butyronitrile (204 mg, 1.25 mmol) (prepared following Marco et. al., Tetrahedron, 2000, 56, 2525-31) 2-chloro-3-trifluoromethylphenol (196 mg, 1.0 mmol) and potassium carbonate (172 mg, 1.25 mmol) in acetonitrile (5 ml) was stirred for 1 hour at 95° C. The mixture was shaken between tBuOMe and water and the ethereal phase dried with $Na_2SO_4$, filtered over a silicagel pad and evaporated to give as yellowish oil 2-(2-chloro-3-trifluoromethyl-phenoxy)-butyronitrile; $^1$H-NMR ($CDCl_3$): 1.27 t, 3H, 2.20 m, 2H, 2.40 s, 3H, 4.78 t, 1H, 7.34, d, 1H; 7.39, t, 1H; 7.48 d, 1H.

A mixture of the product obtained above (330 mg, 1 mmol), ethylene diamine (240 mg, 4 mmol) and sodium tetrasulfide (6 mg, 0.035 mmol) was stirred in methanol (5 ml) for 16 hours at 65° C., and then cooled and evaporated. The crude material was mixed with water and extracted with dichloromethane, dried with $Na_2SO_4$, filtered and evaporated. The crude material was purified on silicagel by flash chromatography (eluent: ethylacetate/methanol/triethylamine 95:2.5:2.5) to yield crystalline 2-[1-(2-chloro-3-trifluoromethyl-phenoxy)-propyl]-4,5-dihydro-1H-imidazole of m.p. 102-103° C.; $^1$H-NMR ($CDCl_3$): 1.08 t, 3H, 2.02 m, 2H, 3.64, b, 4H, 4.87 t, 1H, 7.24 to 7.34, 3 aromatic H.

Example 2

2-[1-(2-Chloro-3-difluoromethyl-phenoxy)-propyl]-4,5-dihydro-1H-imidazole

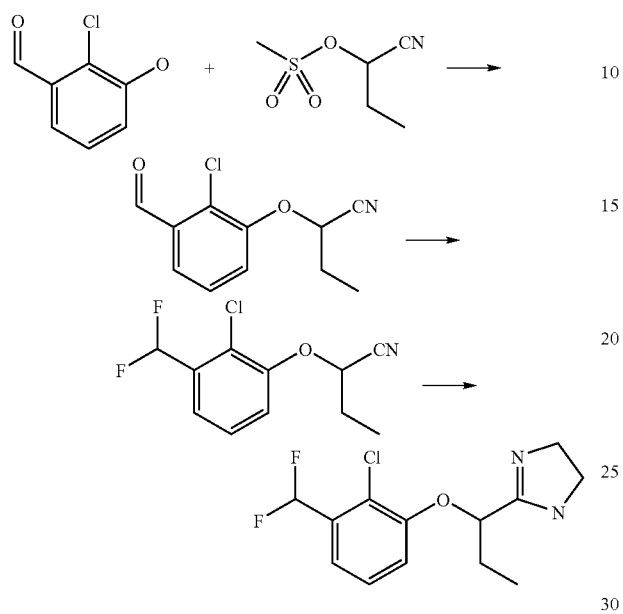

2-Chloro-3-hydroxy-benzaldehyde (1.0 g, 6.4 mmol) was dissolved in 10 ml N-methyl-pyrolidone at 20° C. The resultant yellow solution was degassed with argon. After addition of cesium carbonate (2.29 g, 7.0 mmol) the suspension was stirred for 20 minutes. 2-(methanesulfonyloxy)-butyronitrile (1.56 g, 9.6 mmol) and potassium iodide (0.05 g, 0.05 mmol) were then added and the reaction mixture was heated at 100° C. under microwave irradiation (Initiator™ Sixty, Biotage) for 3 minutes. After adding an additional portion of 2-(methanesulfonyloxy)-butyronitrile (0.52 g, 3.2 mmol) the reaction mixture was once again heated under microwave irradiation at 100° C. for 5 minutes. The reaction was monitored by TLC. On completion, the mixture was poured into water (0° C.) and extracted with ether. The organic layer was separated and washed with NaOH (1N), water and brine and dried with MgSO$_4$. The crude material was purified on silicagel by flash chromatography (ethylacetate/cyclohexane) to give 2-(2-chloro-3-formyl-phenoxy)-butyronitrile as yellow oil; $^1$H-NMR (CDCl$_3$) 1.25, t, 3H, 2.2 m, 2H, 4.81 dd, 1H, 7.4, m, 2H, 7.68 m, 1H, 10.5 s, 1H.

To a solution of 2-(2-chloro-3-formyl-phenoxy)-butyronitrile (0.97 g, 4.3 mmol) in dry CH$_2$Cl$_2$ (30 ml) under N$_2$ was added dropwise diethylaminosulfur trifluoride (DAST, 1.19 g, 7.4 mmol) at −78° C. The cooling was removed and the reaction mixture was stirred overnight. The mixture was poured into water (0° C.) and treated with saturated NaHCO$_3$. After CO$_2$ evolution ceased the mixture was extracted into CH$_2$Cl$_2$ two times. The organic layer was separated, washed with water, brine and dried (MgSO$_4$). The crude product 2-(2-chloro-3-difluoromethyl-phenoxy)-butyronitrile (yellow oil) was directly used without further purification; $^1$H-NMR (CDCl$_3$) 1.25 t, 3H, 2.19 dt, 2H, 4.75 m, 1H, 6.95, t, 1H, 7.27 d, 1H, 7.4 t, 1H, 7.45, d, 1H.

A mixture of 2-(2-chloro-3-difluoromethyl-phenoxy)-butyronitrile (300 mg, 1.2 mmol), ethylene diamine (0.33 ml, 4.9 mmol) and sodium tetrasulfide (11 mg, 0.1 mmol) was stirred for 2 hrs at 50° C., then cooled to room temperature. Cold water (0° C.) was added to the reaction mixture. The resultant suspension was stirred for ca 15 minutes and then filtered, washed and dried to yield 2-[1-(2-chloro-3-difluoromethyl-phenoxy)-propyl]-4,5-dihydro-1H-imidazole (m.p. 96-97° C.); $^1$H-NMR (D$_6$-DMSO) 1.0, t, 3H, 1.8-2.0 m, 2H; 3.42 vbr s, 4H, 4.8, dd, 1H, 6.51, br s, 1H, 7.2, t, 1H, 7.25, d, 1H, 7.32, d, 1H, 7.43, t, 1H.

Example 3

2-[1-(2-Chloro-3-ethynyl-phenoxy)-propyl]-4,5-dihydro-1H-imidazole

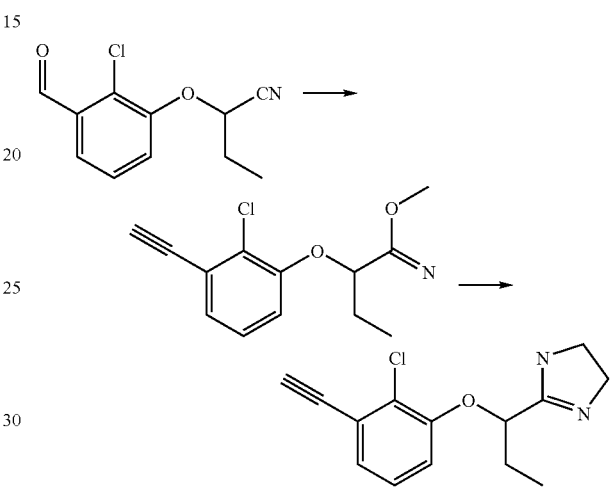

Dimethyl-1-diazo-2-oxypropylphosphonate (0.48 g, 2.5 mmol) was added to a solution of 2-(2-chloro-3-formyl-phenoxy)-butyronitrile (0.4 g, 1.8 mmol) in MeOH (40 ml) at room temperature under argon. The solution was cooled to 0° C. and K$_2$CO$_3$ was added. After the addition stirring was continued for 48 h at room temperature. Reaction mixture was then poured into cold water (0° C.) and extracted twice with ethylacetate. The combined organic layers were dried with MgSO$_4$ and evaporated. The crude product was chromatographed on silica with ethylacetate/cyclohexane to yield 2-(2-chloro-3-ethynyl-phenoxy)-butyrimidic acid methyl ester (0.32 g, light yellow oil); $^1$H-NMR (CDCl$_3$) 1.05 t, 3H, 1.85-2.03 m, 2H, 3.39, s, 1H, 4.52 dd, 1H, 6.78 d, 1H, 7.12 t, 1H, 7.19 d, 1H, 7.72, br s, 1H.

Ethylene diamine (30 mg, 0.5 mmol) was dissolved in dry ethanol (1.9 ml). The solution was cooled to 0° C. and 2-(2-chloro-3-ethynyl-phenoxy)-butyrimidic acid methyl ester (100 mg, 0.4 mmol) was added. After 1 h a solution of concentrated HCl (few drops) in ethanol (0.9 ml) was added and the reaction mixture was stored overnight at 0° C. The reaction mixture was then diluted with a further portion of ethanol (1.6 ml) and heated to 75° C. for 5 h. After cooling to room temperature a precipitate was formed that was filtered and discarded. The filtrate was evaporated and treated with CHCl$_3$. Another precipitate was formed, which was filtered again. Finally, the CHCl$_3$ phase was evaporated to yield 2-[1-(2-chloro-3-ethynyl-phenoxy)-propyl]-4,5-dihydro-1H-imidazole; $^1$H-NMR (CDCl$_3$) 1.08 t, 3H, 1.9-2.1 m, 2H, 3.10-3.9, vbr s, 4H, 3.39, s, 1H, 4.85 dd, 1H, 7.05 d, 1H, 7.1-7.2, m, 2H.

Example 4

This Example illustrates the pesticidal/insecticidal properties of compounds of formula (I). The compounds numbers are those of the characterising data tables. Tests against the following pests *Heliothis virescens, Myzus persicae,* and *Tetranychus urticae* were performed as described below:

4.1 *Heliothis Virescens* (Tobacco Budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation.

The following compounds gave 100% control of *Heliothis virescens:* 1.006, 1.015, 1.021, 1.034 and 1.036. The following compounds gave 80% control of *Heliothis virescens:* 1.008, 1.014, 1.023, 1.028, 1.029, 1.033 and 1.037. The following compounds gave 50% control of *Heliothis virescens:* 1.001, 1.011, 1.022 and 1.027. The following compounds gave 0% control of *Heliothis virescens:* 1.002, 1.003, 1.004, 1.005, 1.007, 1.009, 1.010, 1.012, 1.013, 1.016, 1.017, 1.018, 1.019, 1.020, 1.024, 1.025, 1.030, 1.031, 1.032 and 1.035. The following compound was not tested against *Heliothis virescens:* 1.026

4.2 *Myzus Persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality.

The following compounds gave 100% control of *Myzus persicae:* 1.001, 1.002, 1.003, 1.006, 1.014, 1.015, 1.016, 1.020, 1.021, 1.022, 1.023, 1.028, 1.030, 1.031, 1.032, 1.033, 1.036 and 1.037. The following compounds gave 80% control of *Myzus persicae:* 1.024 and 1.027. The following compounds gave 50% control of *Myzus persicae:* 1.004 and 1.011. The following compounds gave 0% control of *Myzus persicae:* 1.005, 1.007, 1.008, 1.009, 1.010, 1.012, 1.013, 1.017, 1.018, 1.019, 1.025, 1.034 and 1.035. The following compounds were not tested against *Myzus persicae:* 1.026 and 1.029.

4.3 *Myzus Persicae* (Green Peach Aphid):

Roots of pea seedlings, infested with an aphid population of mixed ages, were placed directly in the test solutions of 24 ppm. 6 days after introduction, samples were checked for mortality.

The following compounds gave 100% control of *Myzus persicae:* 1.001 and 1.028. The following compounds gave 80% control of *Myzus persicae:* 1.002, 1.006, 1.016, 1.020, 1.030 and 1.031. The following compounds gave 50% control of *Myzus persicae:* 1.014, 1.015, 1.024, 1.032 and 1.037. The following compounds gave 0% control of *Myzus persicae:* 1.003, 1.005, 1.013, 1.021, 1.023, 1.027, 1.033 and 1.036. The following compounds were not tested: 1.004, 1.007, 1.008, 1.009, 1.010, 1.011, 1.012, 1.017, 1.018, 1.019, 1.022, 1.025, 1.026, 1.029, 1.034 and 1.035.

4.4 *Tetranychus Urticae* (Two-Spotted Spider Mite):

4.4.1 Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave 100% control of *Tetranychus urticae:* 1.001, 1.002, 1.006, 1.015, 1.016, 1.020, 1.021, 1.024, 1.027, 1.028, 1.030, 1.031, 1.036 and 1.037. The following compounds gave 80% control of *Tetranychus urticae:* 1.014, 1.022 and 1.033. The following compound gave 50% control of *Tetranychus urticae:* 1.025. The following compounds gave 0% control of *Tetranychus urticae:* 1.003, 1.004, 1.005, 1.007, 1.008, 1.009, 1.010, 1.011, 1.012, 1.013, 1.017, 1.018, 1.019, 1.023, 1.032, 1.034 and 1.035. The following compounds were not tested against *Tetranychus urticae:* 1.026 and 1.029

4.4.2 In a further test, the efficacy of one of the compounds giving 100% control in Example 4.4.1 above was compared to the efficacy of imidazoline compounds from the prior art (compounds A and B).

Bean leaf discs on agar in 24-well microtiter plates were sprayed with test solutions at an application rate of 12.5 ppm. After drying, the leaf discs are infested with mite populations of mixed ages. 8 days later, discs are checked for egg mortality, larval mortality, and adult mortality. The results are shown below in Table 5.

As can be seen from the Table, compounds 1.001 gives superior control of *T. urticae* in comparison to compounds A and B.

TABLE 5

Efficacy of compounds of formula (X) against *T. Urticae,* wherein $R^1$, $R^2$ and $R^3$ have the values given.

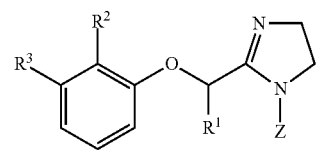

(X)

| Compound | $R^1$ | $R^2$ | $R^3$ | Control % |
|---|---|---|---|---|
| 1.001 | $CH_2CH_3$ | Cl | $CF_3$ | 80 |
| B | $CH_2CH_3$ | Cl | $CH_3$ | 50 |
| A | $CH_2CH_3$ | Cl | Cl | 0 |

The invention claimed is:

1. A compound of formula (I):

(I)

and salts and N-oxides thereof, wherein:

$R^1$ is $C_{1-10}$ alkyl;

$R^2$ is chloro, bromo or iodo;

$R^3$ is $C_{1-5}$ haloalkyl; and

Z is hydrogen or C(O)OtButyl.

2. The compound according to claim 1, wherein $R^3$ is $C_{1-4}$ haloalkyl.

3. The compound according to claim 2, wherein $R^3$ is $C_1$ haloalkyl.

4. The compound according to claim 3, wherein $R^3$ is fluoromethyl, difluoromethyl or trifluoromethyl.

5. The compound according to claim 1, wherein $R^1$ is $C_{1-5}$ alkyl.

6. The compound according to claim 5, wherein $R^1$ is methyl, ethyl, n-propyl, or iso-propyl.

7. A compound of the formula (4)

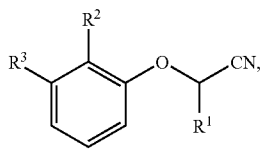

wherein
  $R^1$ is $C_{1-10}$ alkyl;
  $R^2$ is chloro, bromo, iodo or amino; and
  $R^3$ is $C_{2-5}$ alkyl, $C_{1-5}$ haloalkyl, $C_{1-6}$ hydroxyalkyl, $C_{1-5}$ alkoxy-$(C_{1-3})$-alkyl, di-$(C_{1-5}$ alkoxy)-$(C_{1-3})$-alkyl, $C_{1-5}$ alkylthio-$(C_{1-3})$-alkyl; $C_{1-5}$ alkylsulfinyl-$(C_{1-3})$-alkyl; $C_{2-5}$ alkenyl, $C_{1-5}$ haloalkenyl, $C_{2-5}$ alkinyl, $C_{3-6}$ cycloalkyl, $C_{3-6}$ cycloalkenyl, hydroxy, $C_{1-5}$ alkoxy, $C_{1-5}$ haloalkoxy, $C_{1-15}$ alkylthio, $C_{1-5}$ haloalkylthio, formyl, cyano, bromo, or iodo.

8. An insecticidal, acaricidal, nematicidal or molluscicidal composition comprising a compound of claim 1, and an agrochemically suitable inert diluent or carrier.

9. A method of combating and/or controlling a pest selected from the group consisting of insects, acarids, nematodes and molluscs, which comprises applying to said pest, or to the locus of said pest, or to a plant susceptible to attack by said pest, a compound of claim 1.

10. The method according to claim 9, wherein said pest is an insect of the order Hemiptera, Lepidoptera, Coleoptera, Thysanoptera, Diptera, Blattodea, Isoptera, Siphonaptera, Hymenoptera or Orthoptera.

11. The method according to claim 10, wherein said insect is of the order Lepidoptera, Thysanoptera, Isoptera, Siphonoptera, Hymenoptera or Orthoptera.

12. The method according to claim 10, wherein said insect is of the order Hemiptera, Lepidoptera, Coleoptera, Thysanoptera or Diptera.

13. The method according to claim 12, wherein said pest is of the order Hemiptera.

14. The compound according to claim 4, wherein $R^1$ is $C_{1-5}$ alkyl.

15. The compound according to claim 14, wherein $R^1$ is methyl, ethyl, n-propyl, or iso-propyl.

16. An insecticidal, acaricidal, nematicidal or molluscicidal composition comprising a compound of claim 4, and an agrochemically suitable inert diluent or carrier.

17. A method of combating and/or controlling a pest selected from the group consisting of insects, acarids, nematodes and molluscs, which comprises applying to said pest, or to the locus of said pest, or to a plant susceptible to attack by said pest, a compound of claim 4.

18. An insecticidal, acaricidal, nematicidal or molluscicidal composition comprising a compound of claim 15, and an agrochemically suitable inert diluent or carrier.

19. A method of combating and/or controlling a pest selected from the group consisting of insects, acarids, nematodes and molluscs, which comprises applying to said pest, or to the locus of said pest, or to a plant susceptible to attack by said pest, a compound of claim 15.

* * * * *